United States Patent
Hrdlicka et al.

(10) Patent No.: US 7,493,159 B2
(45) Date of Patent: *Feb. 17, 2009

(54) TRIAL NEURO STIMULATOR WITH LEAD DIAGNOSTICS

(75) Inventors: Gregory A. Hrdlicka, Plymouth, MN (US); Robert M. Skime, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 606 days.

This patent is subject to a terminal disclaimer.

(21) Appl. No.: 10/636,487

(22) Filed: Aug. 6, 2003

(65) Prior Publication Data

US 2004/0111130 A1  Jun. 10, 2004

Related U.S. Application Data

(63) Continuation of application No. 09/596,220, filed on Jun. 19, 2000, now Pat. No. 6,687,538.

(51) Int. Cl.
*A61N 1/08* (2006.01)
(52) U.S. Cl. .............................. 607/2; 607/27; 607/37; 607/62; 600/547
(58) Field of Classification Search .............. 607/27, 607/2, 37, 10, 57, 62, 63, 28; 600/547
See application file for complete search history.

(56) References Cited

U.S. PATENT DOCUMENTS

| | | | |
|---|---|---|---|
| 3,911,930 A | | 10/1975 | Hagfors et al. |
| 4,141,367 A | * | 2/1979 | Ferreira .................. 607/27 |
| 4,379,462 A | | 4/1983 | Borkan et al. |
| 4,582,063 A | * | 4/1986 | Mickiewicz et al. ........ 607/46 |
| 4,744,371 A | * | 5/1988 | Harris ..................... 607/117 |
| 4,899,750 A | | 2/1990 | Ekwall |
| 5,003,975 A | | 4/1991 | Hafelfinger et al. |
| 5,354,326 A | | 10/1994 | Comben et al. |
| 5,361,776 A | * | 11/1994 | Samuelson et al. ......... 600/547 |
| 5,417,719 A | | 5/1995 | Hull et al. |
| 5,557,210 A | * | 9/1996 | Cappa et al. ............... 324/539 |

(Continued)

OTHER PUBLICATIONS

Medtronic, "Model 3625 Screener Brochure," 1991.
Medtronic, "Implantable Neurostimulation Systems Brochure," 1998.

*Primary Examiner*—Kennedy J Schaetzle
(74) *Attorney, Agent, or Firm*—Shumaker & Sieffert, P.A.

(57) ABSTRACT

A medical device known as a trial neuro stimulator with a diagnostics module to determine whether the therapy lead is operational for delivering stimulation therapy to improve operation in areas such as reliability and patient comfort is disclosed. The trial neuro stimulator is typically used to test the efficacy of neuro stimulation before implanting an implantable neuro stimulator in a patient. The trial neuro stimulator has a processor, memory, system reset, telemetry module, recharge module, power management module, power source, therapy module, therapy measurement module, and diagnostics module. The diagnostics module can be a lead sensor, a software detector using therapy lead measurements from the therapy measurement module, or, a combination of both the lead sensor and software detector to detect whether the therapy lead is operational. A method for diagnosing whether a therapy lead is operational is also disclosed.

12 Claims, 18 Drawing Sheets

U.S. PATENT DOCUMENTS

| | | |
|---|---|---|
| 5,814,088 A | 9/1998 | Paul et al. |
| RE35,987 E | 12/1998 | Harris et al. |
| 5,891,179 A | 4/1999 | Er et al. |
| 5,897,577 A | 4/1999 | Cinbis et al. |
| 6,066,165 A | 5/2000 | Racz |
| H1929 H | 12/2000 | Citak |
| 6,317,633 B1 | 11/2001 | Jorgenson et al. |
| 6,516,227 B1 * | 2/2003 | Meadows et al. ............. 607/46 |

* cited by examiner

TRIAL NEURO STIMULATOR WITH LEAD DIAGNOSTICS

RELATED APPLICATION

The present application is a continuation of U.S. application Ser. No. 09/596,220, filed Jun. 19, 2000, which issued as U.S. Pat. No. 6,687,538 on Feb. 3, 2004, the entire content of which is incorporated herein by reference.

BACKGROUND OF THE INVENTION

This disclosure relates to a medical device and more specifically to a neuro stimulator that produces an electrical stimulation signal used to influence the human body.

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. One type of medical device that can be used is an Implantable Neuro Stimulator (INS)

An INS generates an electrical stimulation signal that is used to influence the human nervous system or organs. Electrical contacts carried on the distal end of a lead are placed at the desired stimulation site such as the spine and the proximal end of the lead is connected to the INS. The INS is then surgically implanted into an individual such as into a subcutaneous pocket in the abdomen, pectoral region, or upper buttocks area. The INS can be powered by an internal source such as a battery, or by an external source such as a radio frequency transmitter. A clinician programs the INS with a therapy using a programmer. The therapy configures parameters of the stimulation signal for the specific patient's therapy. An INS can be used to treat conditions such as pain, incontinence, movement disorders such as epilepsy and Parkinson's disease, and sleep apnea. Additional therapies appear promising to treat a variety of physiological, psychological, and emotional conditions. Before an INS is implanted to deliver a therapy, an external screener that replicates some or all of the INS functions is typically connected to the patient to evaluate the efficacy of the proposed therapy.

When a screener is used to test the efficacy of a stimulation therapy, the screener including its leads should be fully operational to correctly assess the efficacy of the proposed stimulation therapy. When previous screeners were operationally connected to a patient, the clinician would verify that the leads were operational. Once the patient left the clinician's office the stimulation therapy efficacy could be reduced by stimulation energy not reaching the targeted site due to leads that have become inoperative through a nonconformance, disconnection, or open connection, and the patient might not become aware of the inoperative lead until the next visit with a clinician. In other situations the leads may become temporarily inoperative which can subject the patient to abrupt initiation and cessation of stimulation therapy causing patient discomfort and unreliable indications of efficacy. Unreliable efficacy testing data can result in some patients not receiving an INS when the therapy would have treated their medical condition, and other patients receiving an INS when the therapy would not effectively treat their medical condition. An example of a screener is shown in a brochure titled "Model 3625 Screener" available from Medtronic, Inc., Minneapolis, Minn., and examples of some neuro stimulation products and related components are shown and described in a brochure titled "Implantable Neurostimulation Systems" also available from Medtronic, Inc.

For the foregoing reasons there is a need for a screener that can diagnose inoperative leads to improve operation in areas such as reliability, and patient comfort.

SUMMARY OF THE INVENTION

A trial neuro stimulator for delivery of stimulation therapy has a lead diagnostic module coupled to a therapy module connector and is coupleable to a therapy lead to improve operation in areas such as reliability and patient comfort. The lead diagnostic module is configured for determining whether the therapy lead is operational to deliver stimulation signals. The therapy module is operated according to the therapy program to produce stimulation signals. The therapy program is contained in memory and executed by a processor coupled to memory.

DETAILED DESCRIPTION OF THE PREFERRED EMBODIMENTS

Figure 1:
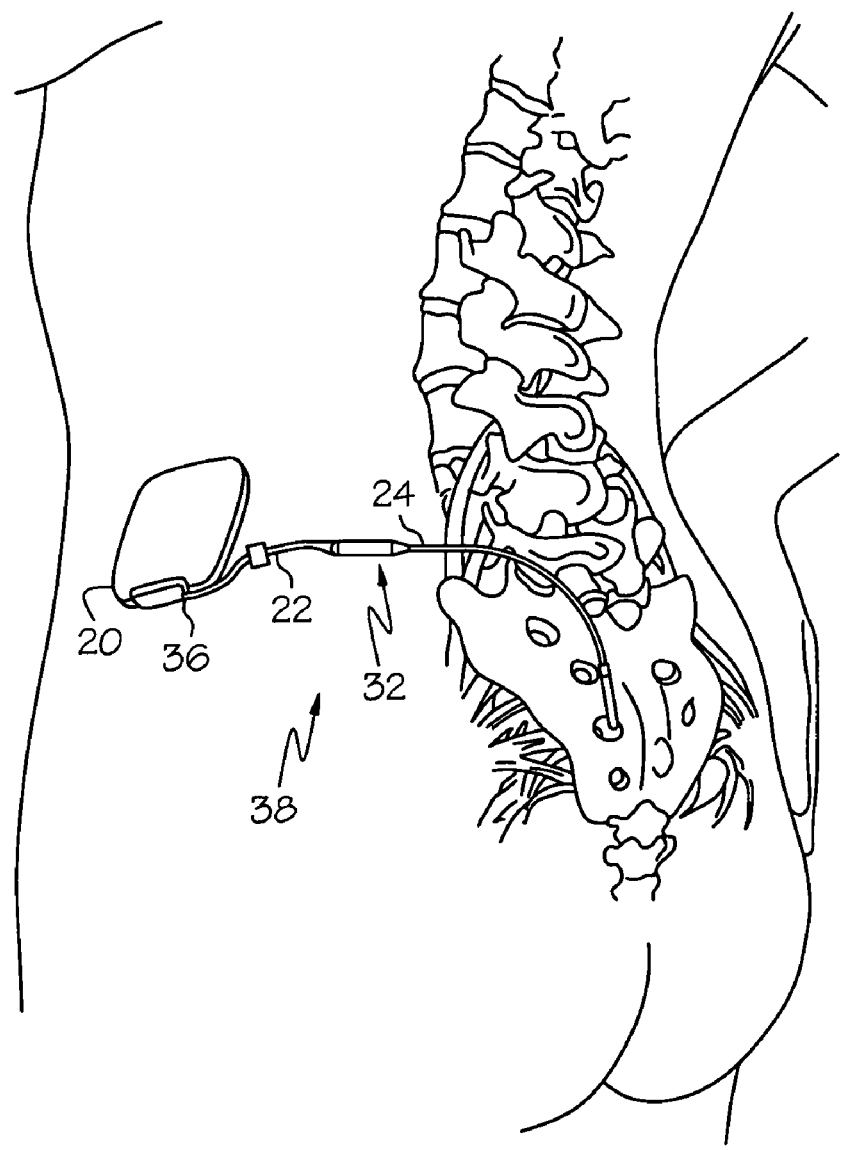
FIG. 1 shows an environment of a Trial Neuro Stimulator (TNS)
Figure 1:
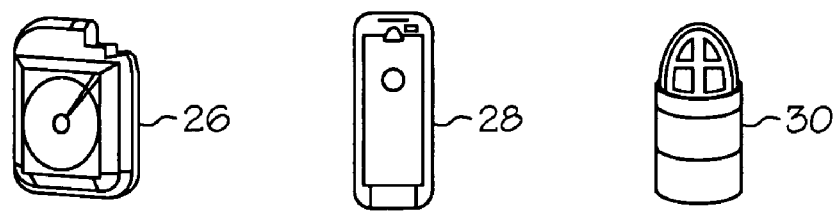

FIG. 1 shows the general environment of a Trial Neuro Stimulator (TNS) 20 medical device including a lead extension 22, and stimulation lead 24, an Implantable Neuro Stimulator (INS) 26, a physician programmer 28, and a patient programmer 30. The stimulation lead 24 is one or more insulated electrical conductors with a connector 32 on the proximal end and electrical contacts 34 on the distal end.

Some stimulation leads 24 are designed to be inserted into a patient percutaneously, such as the Model 3487A Pisces-Quad® lead available from Medtronic, Inc. of Minneapolis Minn., and some leads 24 are designed to be surgically implanted, such as the Model 3993 Specify® lead also available from Medtronic. Although the lead connector 32 can be connected directly to the INS 26, typically the lead connector 32 is connected to a lead extension 22 which can be either temporary for use with a TNS 20 or permanent for use with an INS 26. The lead extension 22, such as a Model 7495 available from Medtronic, is then connected to the INS 26. The TNS 20 functions similarly to the INS 26 but is not designed for implantation. The TNS 20 is used to test the efficacy of stimulation therapy for the patient before the INS 26 is surgically implanted. The TNS 20 is typically connected to a screening cable 36 and the screening cable 36 is connected to the percutaneous lead extension 22 which is connected to the simulation lead 24. The physician programmer 28, also known as a console programmer, uses telemetry to communicate with the implanted INS 26, so a clinician can program and manage a patient's therapy stored in the INS 26 and troubleshoot the patient's INS 26 system. An example of a physician programmer 28 is a Model 7432 Console Programmer available from Medtronic. The patient programmer 30 also uses telemetry to communicate with the INS 26, so the patient can manage sonic aspects of her therapy as defined by the clinician. An example of a patient programmer 30 is a Model 7434 Itrel® 3 EZ Patient Programmer available from Medtronic.

Implantation of an Implantable Neuro Stimulator (INS) 26 typically begins with implantation of at least one stimulation lead 24 usually while the patient is under a local anesthetic, The stimulation lead 24 can either be percutaneously or surgically implanted. Once the stimulation lead 24 has been implanted and positioned, the stimulation lead's 24 distal end is typically anchored into position to minimize movement of the stimulation lead 24 after implantation. The stimulation lead's 24 proximal end can be configured to connect to a lead extension 22. The lead extension 22 can be a percutaneous lead extension with a proximal end that is external to the body and configured to connect to either a screening cable 36 or directly to the Trial Neuro Stimulator (TNS) 20. The operational lead configuration is referred to as the therapy lead 38 and includes a stimulation lead 24 and can, include a lead extension 22, or a lead extension 22 and a screening cable 36. During the screening period the TNS 20 is programmed with a therapy and the therapy is often modified to optimize the therapy for the patient. Once screening has been completed and efficacy has been established, the lead's 24 proximal end or the lead extension 22 proximal end is connected to the INS 26. The INS 26 is programmed with a therapy and then implanted in the body typically in a subcutaneous pocket at a site selected after considering clinician and patient preferences. The clinician periodically uses a console programmer 28 to communicate with the implanted INS 26 to manage the patient therapy and collect INS 26 data. The patient uses the patient programmer 30 to communicate with the implanted INS 26 for purposes such as to make therapy adjustment that have been programmed by the clinician, recharge the INS 26 power source when the INS 26 is configured for recharging, record diary entries about the effectiveness of the therapy, and turning the INS 26 "on" and "off". Both the console programmer 28 and patient programmer 30 can have an antenna locator that indicates when the telemetry head is aligned closely enough with the implanted INS 26 for adequate telemetry.

Figure 2:
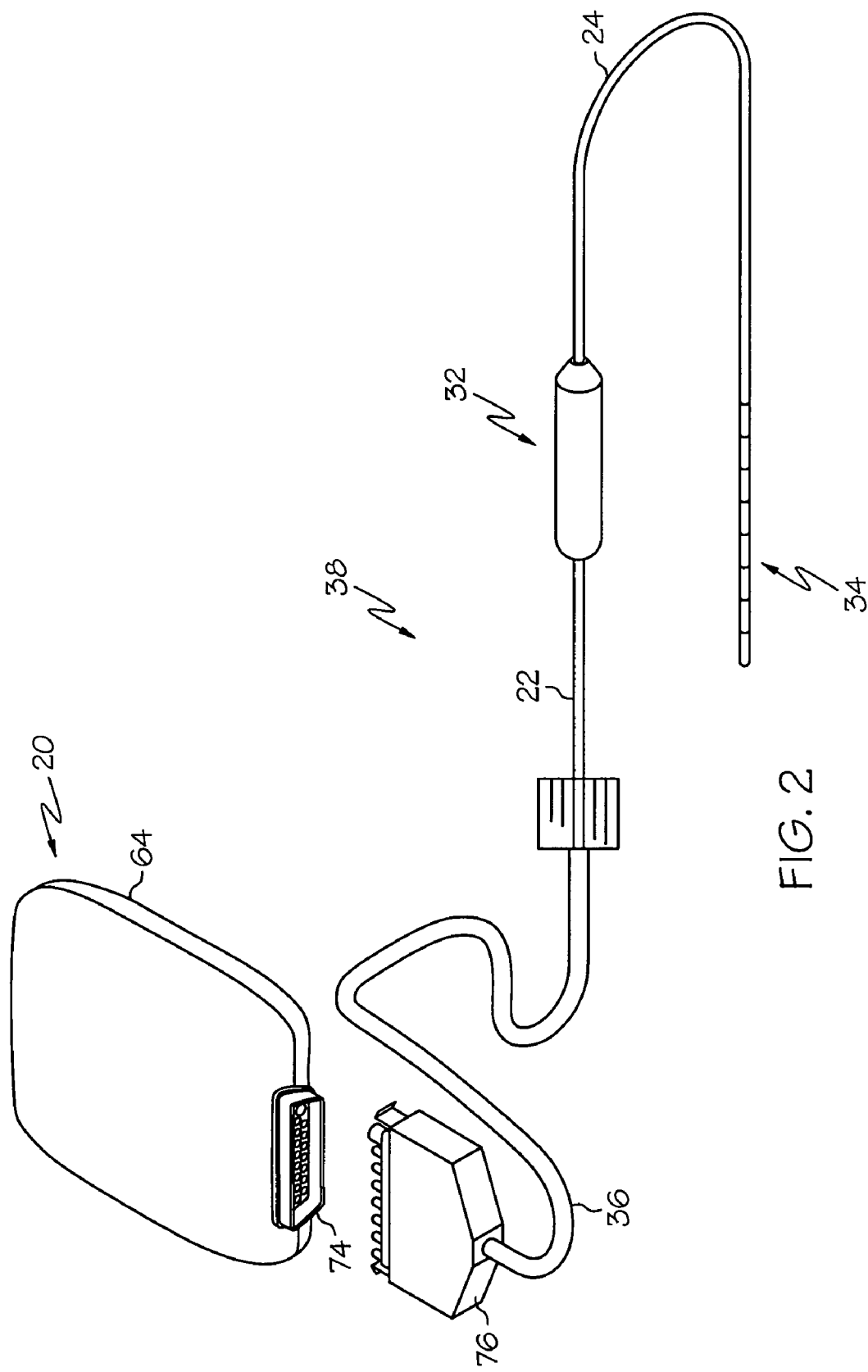
FIG. 2 shows a TNS with therapy lead embodiment.
Figure 3A:
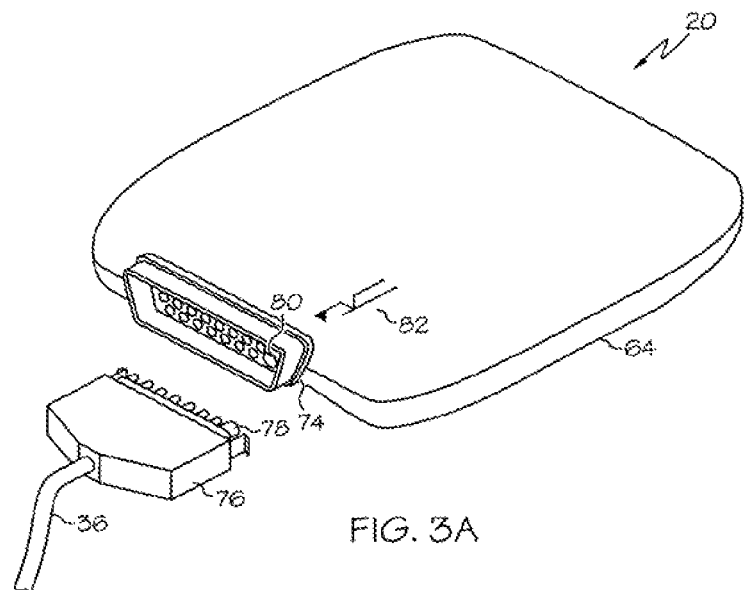
FIG. 3a shows a TNS embodiment.
Figure 3B:
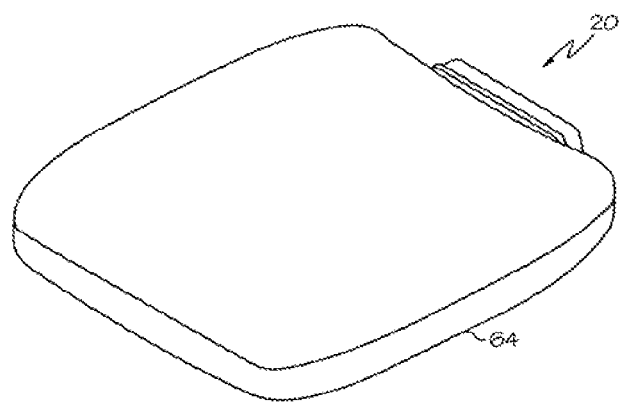
FIG. 3b shows another view of the TNS embodiment.
Figure 4:
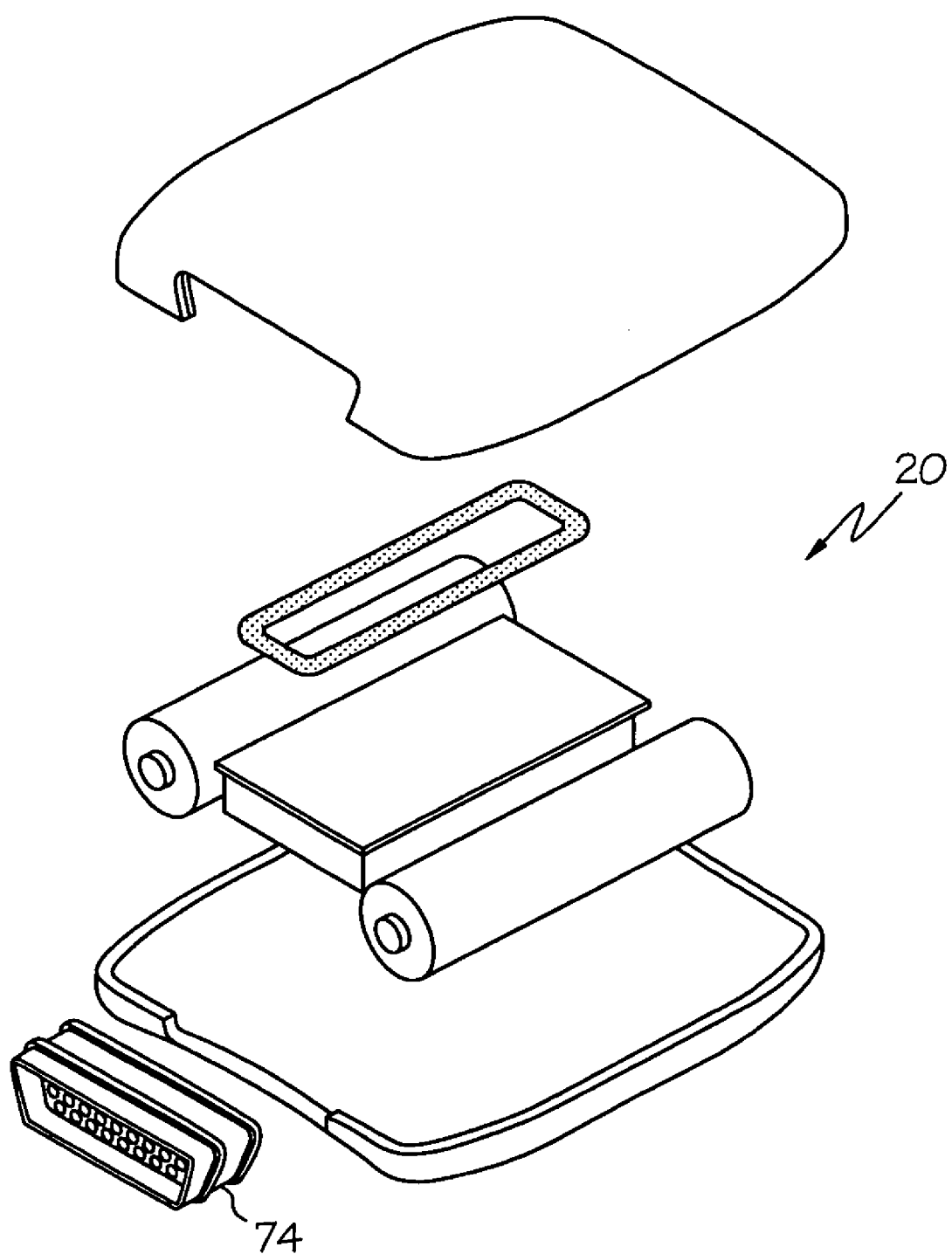
FIG. 4 shows an exploded view of the TNS embodiment.
Figure 5:
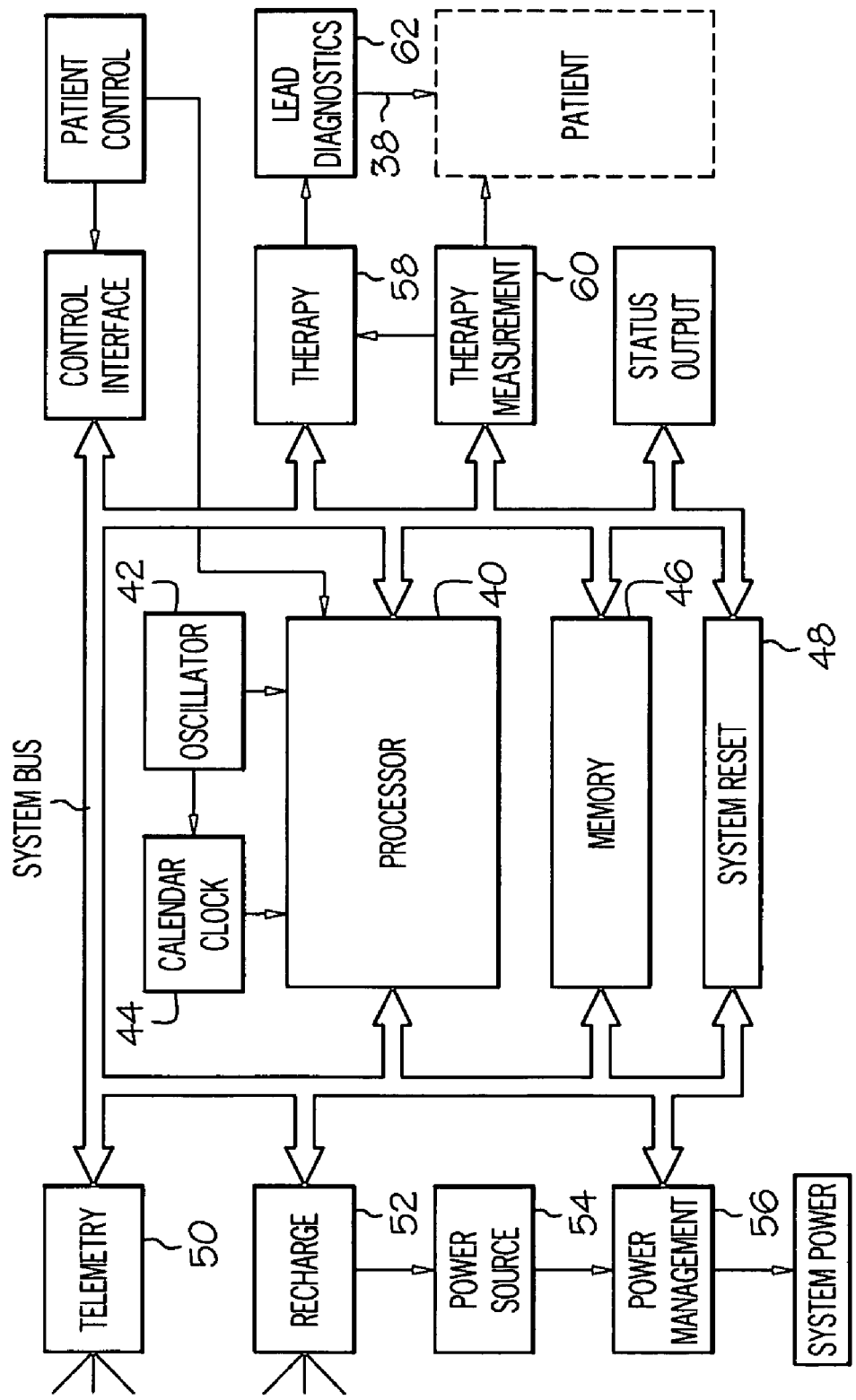
FIG. 5 shows a TNS block diagram embodiment.

FIG. 2 shows a Trial Neuro Stimulator (TNS) 20 with a screening cable 36, lead extension 22, and a stimulation lead 24 having electrical contacts 34. FIGS. 3a and 3b show views of a TNS 20 embodiment. FIG. 4 shows an exploded view of a TNS 20 embodiment. FIG. 5 shows a block diagram of a TNS 20 embodiment. The TNS 20 generates a programmable electrical stimulation signal that is used to evaluate the efficacy of using electrical stimulation to treat a patient condition. The TNS 20 comprises a processor 40 with an oscillator 42, a calendar clock 44, memory 46, and system reset 48, a telemetry module 50, a recharge module 52, a power source 54, a power management module 56, a therapy module 58, a therapy measurement module 60, and a lead diagnostics module 62. In non-rechargeable versions of the TNS 20, the recharge module 52 can be omitted. All components can be configured on one or more Application Specific Integrated Circuits (ASICs), or a combination of ASICs and commercially available integrated circuits except the power source 54. Also, all components are connected to bi-directional data bus that is non-multiplexed with separate address and data lines except the oscillator 42, the calendar clock 44, and the power source 54. The processor 40 is a low power microcontroller such as a Motorola 68HC11 synthesized core operating with a compatible instruction set. The oscillator 42 operates at a frequency compatible with the processor 40, associated components, and energy constraints such as in the range from 10.0 KHz to 4.0 MHz. The calendar clock 44 keeps track of the time since a fixed date fox date/time stamping of events and for therapy control such as circadian rhythm linked therapies. The memory 46 includes memory 46 sufficient operation of the TNS 20 such as volatile Random Access Memory (RAM) for example Static RAM, nonvolatile Read Only Memory (ROM), Electrically Eraseable Programmable Read Only Memory (EEPROM) for example Flash EEPROM, and register arrays configured on ASICS. Direct Memory Access (DMA) is available to selected modules such as the telemetry module 50, so the telemetry module 50 can request control of the data bus and write data directly to memory 46 bypassing the processor 40. The system reset 48 controls operation of ASICs and modules during power-up and power-down of the TNS 20, so the ASICs and modules registers can be loaded and brought on-line or off-line in a stable condition. The TNS 20 can be configured in a variety of versions by removing modules not necessary for the particular configuration and by adding additional components or modules. Primary cell, non-rechargeable, versions of the TNS 20 will not include some or all of the components in the recharge module 52. All components of the TNS 20 are contained within or carried on a housing 64.

Figure 6:
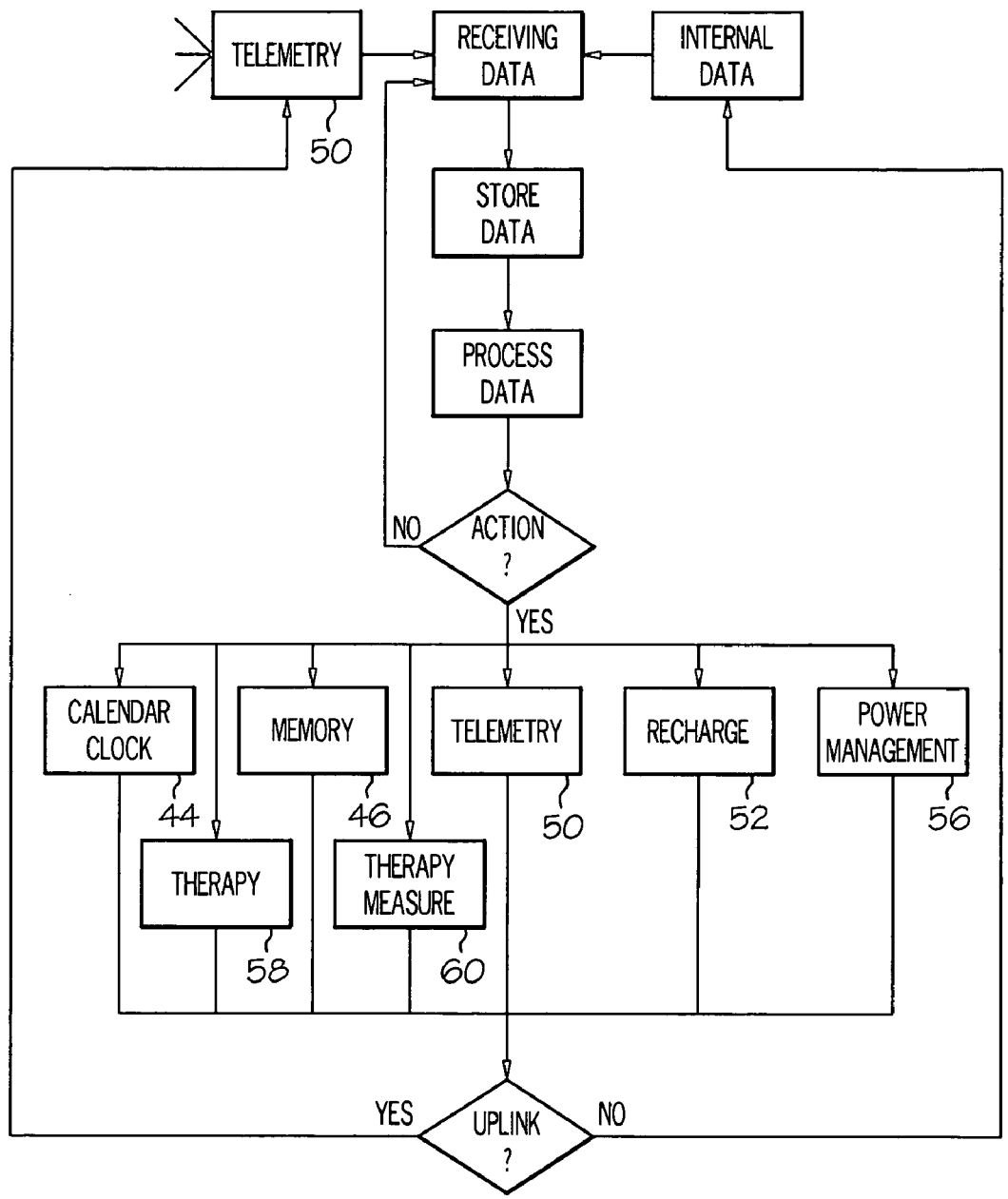
FIG. 6 shows a TNS basic operation flowchart embodiment.

FIG. 6 shows a basic TNS 20 operation flowchart. Operation begins when the processor 40 receives data from either telemetry or from an internal source in the TNS 20. The received data is then stored in a memory 46 location. The data is processed by the processor 40 to identify the type of data and can include further processing such as validating the integrity of the data. After the data is processed, a decision is made whether to take an action. If no action is required, the TNS 20 stands by to receive data. If an action is required, the action will involve one or more of the following modules or components: calendar clock 44, memory 46, telemetry 50, recharge 52, power management 56, therapy 58, and therapy measurement 60. An example of an action would be to modify a programmed therapy. After the action is taken, a decision is made whether to prepare the action to be communicated, known as uplinked, to a patient programmer 30 or console programmer 28 through the telemetry module 50. If the action is uplinked, the action is recorded in the patient programmer 30 or console programmer 28. If the action is not uplinked, the action is recorded internally within the TNS 20.

Figure 7:
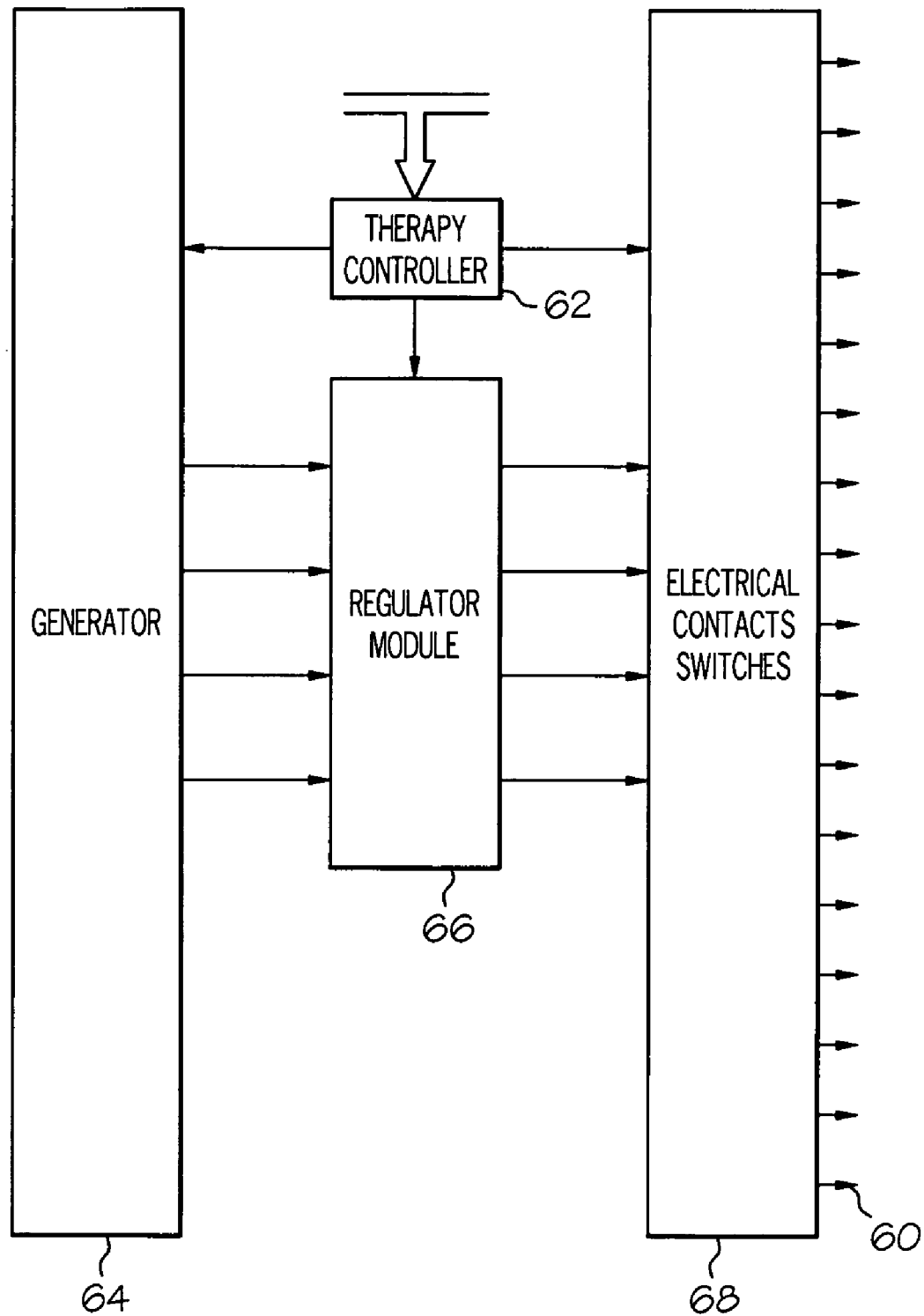
FIG. 7 shows a therapy module block diagram embodiment.

FIG. 7 shows a therapy module 58 block diagram. The therapy module 58 generates a programmable stimulation signal 60 that is transmitted through one or more leads 24 to electrical contacts 34 implanted in the patient. The therapy module 58 comprises a therapy controller 62, a generator 64, a regulator module 66, and electrical contact switches 68. The therapy controller 62 can be a state machine having registers and a timer. The therapy controller 62 controls the generator 64 and regulator module 66 to create a stimulation signal 60. The generator 64 assembles capacitors that have been charged by the power source 54 to generate a wide variety of voltages or currents. The regulator module 66 includes current/voltage regulators that receive a therapy current or voltage from the generator controller 64 and shape the stimulation signal 60 according to the therapy controller 62. The electrical contact switches 68 are solid state switches such as Field Effect Transistor (FET) switches. The electrical contacts 34 are carried on the distal end of a lead 24 and deliver the stimulation signal 60 to the body. Additional switches can be added to provide a stimulation signal 60 to additional electrical contacts 34. The therapy module 58 can deliver individual output pulses in the range from 0.0 Volts to 15.0 Volts into a range from about 100 Ohms to 20.0 K Ohms impedance throughout the capabilities of its operating parameter range to any combination of anodes and cathodes of up to eighteen electrical contacts 34 for any given stimulation signal 60.

Figure 8:
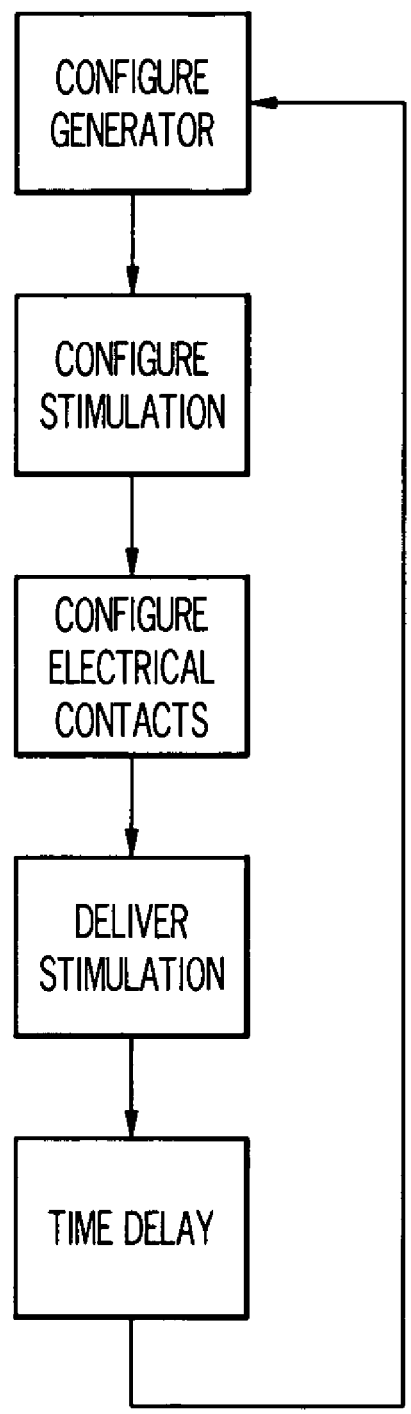
FIG. 8 shows a therapy module operation flowchart embodiment.

FIG. 8 shows therapy module 58 operation with a flowchart. The therapy begins with the therapy controller 62 configuring the generator 64 according to the therapy program to provide appropriate voltage to the regulator module 66. The therapy controller 62 also configures the regulator module 66 to produce the stimulation signal 60 according to the therapy program. The therapy controller 62 also configures the electrical contacts 34 to so the stimulation signal 60 is delivered to the electrical contacts 34 specified by the therapy program. The stimulation signal 60 is delivered to the patient. After the stimulation signal 60 is delivered to the patient, most therapies include a time delay for stimulation pulse recharge before the next stimulation signal 60 is delivered.

Figure 9:
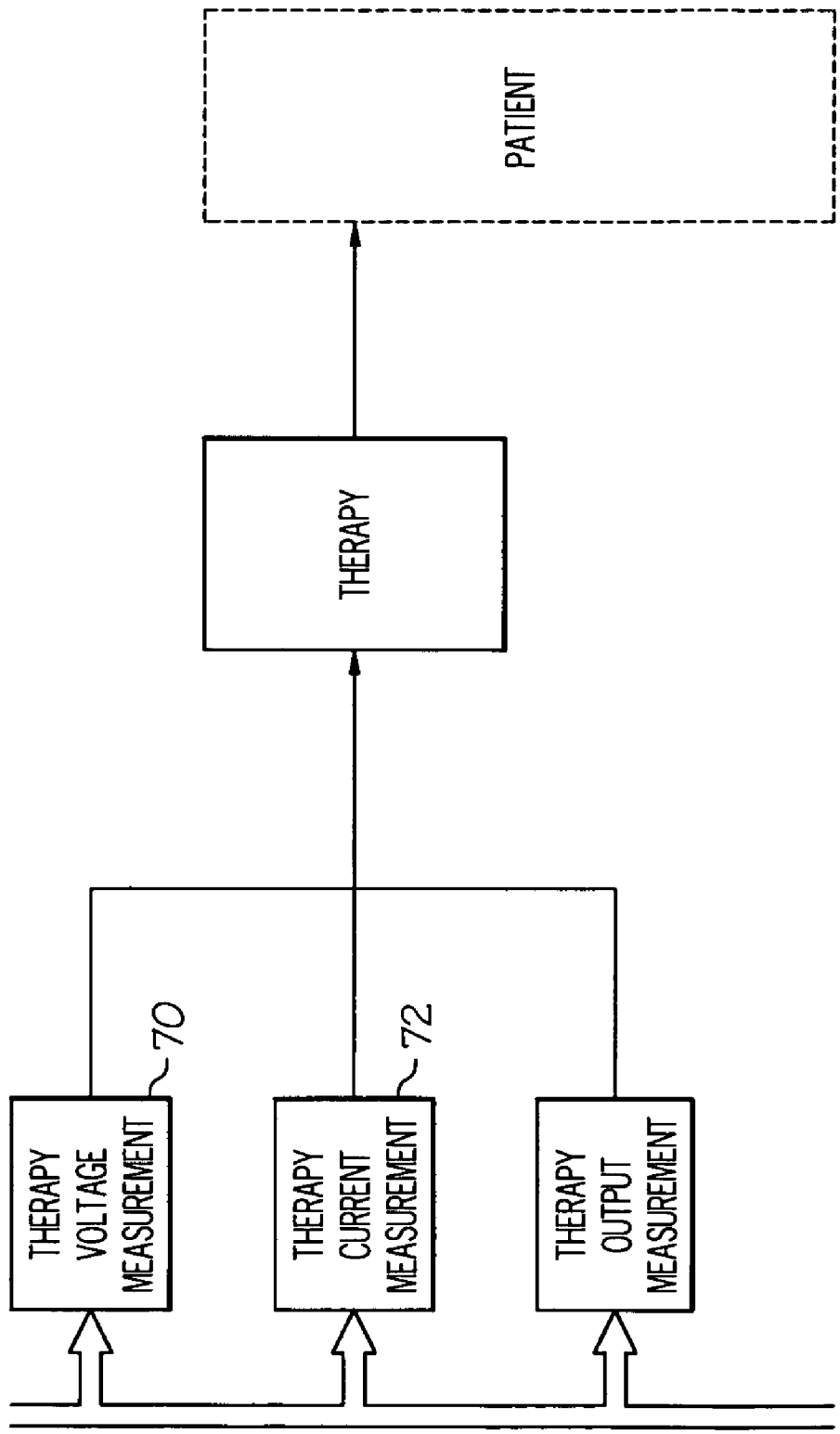
FIG. 9 shows a therapy measurement block diagram embodiment.

FIG. 9 shows a therapy measurement module 60 block diagram. The therapy measurement module 60 measures one or more therapy parameters at the therapy module 58 to determine whether the therapy is appropriate. The therapy measurement module 60 includes a therapy voltage measurement 70, and a therapy current measurement 72. The therapy voltage measurements and therapy current measurements are taken periodically to perform therapy calculations such as therapy lead 38 impedance. More specifically therapy lead 38 impedance is typically measured by measuring stimulation current and stimulation voltage, or stimulation charge.

Figure 10:
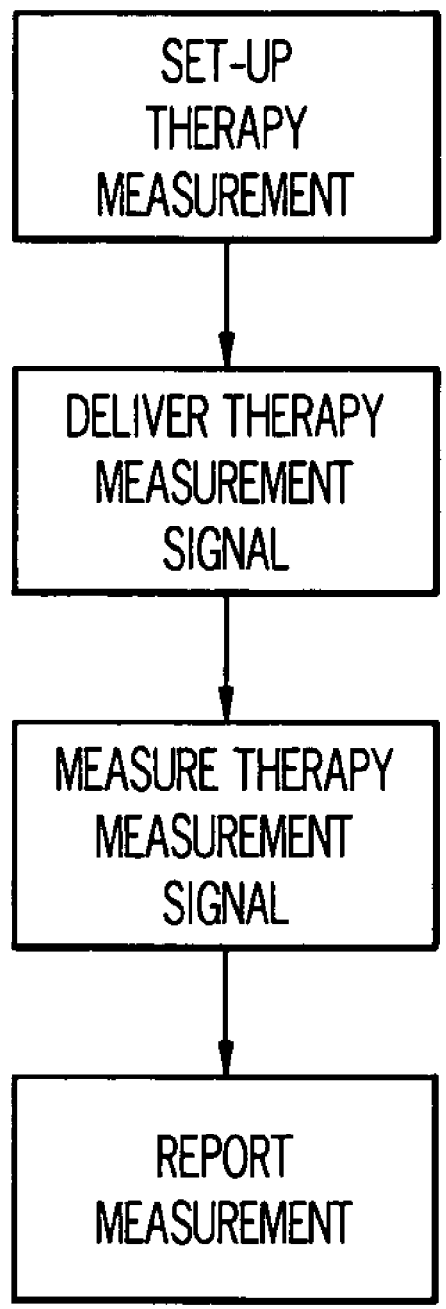
FIG. 10 shows a therapy measurement operation flowchart embodiment.

FIG. 10 shows a therapy measurement module 60 operation flowchart. The therapy measurement operation begins by processor 40 setting up parameters of the therapy measurement to be taken such as which stimulation signal parameter to measure and at which electrical contacts to make the measurement. Before a therapy measurement is taken a threshold determination can be made whether a therapy measurement is needed. When a therapy measurement is desired, the therapy is delivered and then the therapy measurement is taken. The therapy measurement is reported to the processor 40 for action or storage in memory 46. Examples of some actions that might be take when the therapy measurement is reported include an adjustment to the therapy, notification that the therapy lead is not fully operational or inoperative, and a diary entry in memory that can be evaluated by the clinician at a later time.

Figure 11:
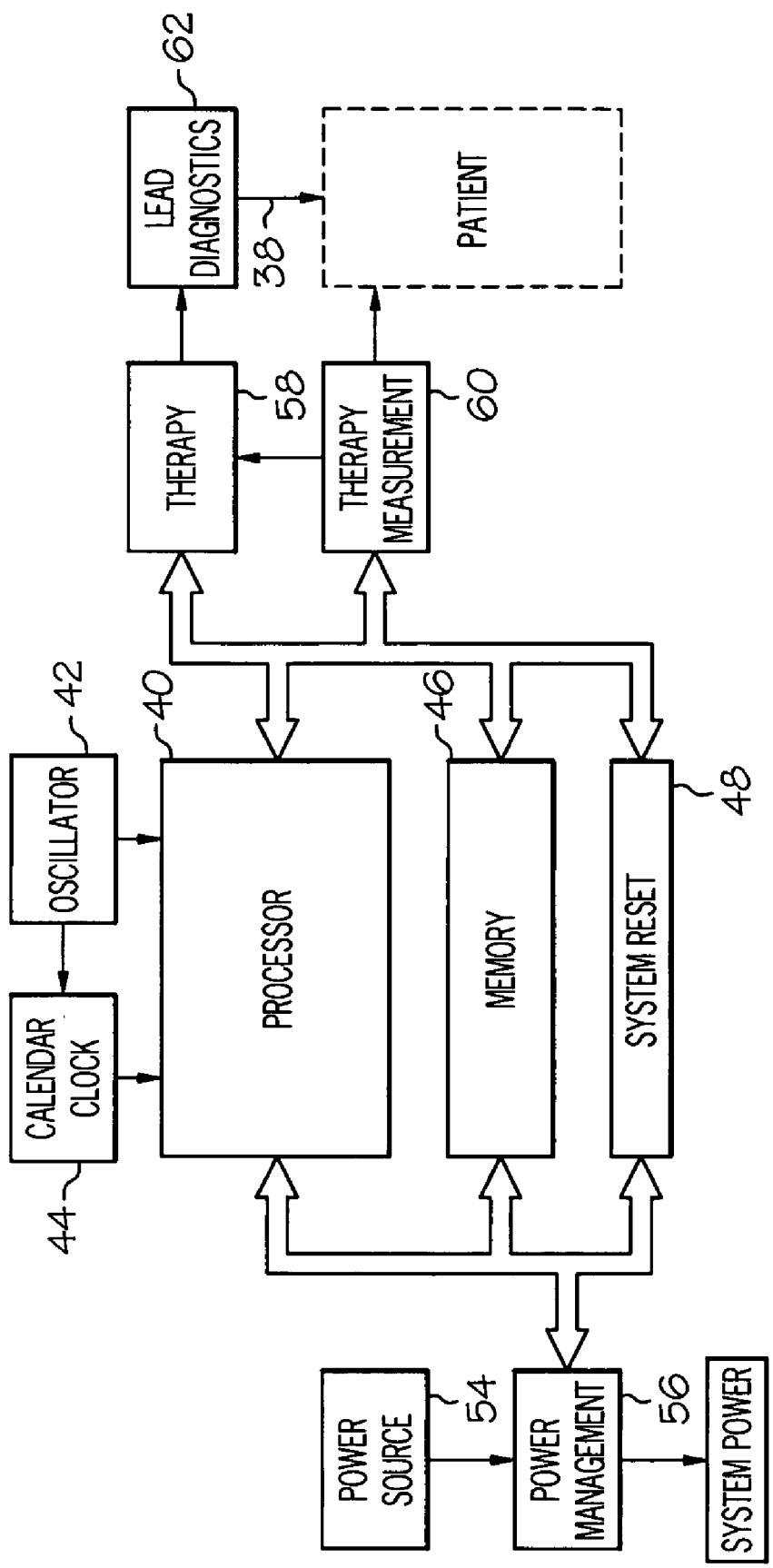
FIG. 11 shows a TNS with lead diagnostics embodiment.
Figure 12:
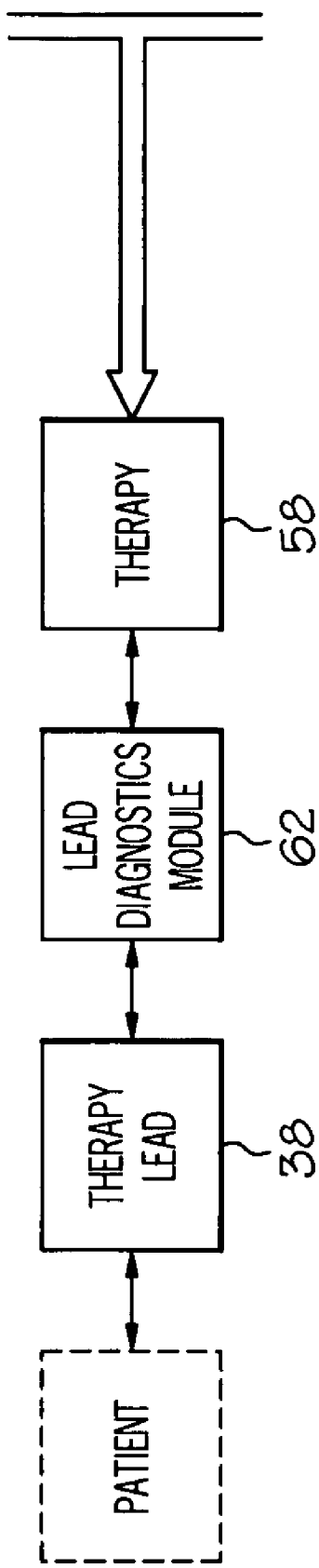
FIG. 12 shows a lead diagnostics module and related components embodiment.

FIG. 11 shows a Trial Neuro Stimulator (INS) 20 with lead diagnostics block diagram embodiment, and FIG. 12 shows a TNS 20 with therapy lead embodiment. The TNS 20 with diagnostics for screening a patient to evaluate the efficacy of neuro stimulation comprises a processor 40, memory 46, a therapy module 58, and a lead diagnostics module 62. The TNS 20 can also include additional components such as an annunciator. The processor 40 and memory 46 containing a therapy program are similar to those disclosed under the FIG. 4 discussion. The therapy program is similar to that disclosed under the FIGS. 1, 7, and 8 discussion. The therapy module 58 is operated according to the therapy program to produce stimulation signals 60. The therapy module 58 has a therapy module connector 74 coupled to the lead diagnostic module 62 which is coupleable to a therapy lead 38. The lead diagnostic module 62 is configured for determining whether the therapy lead 38 is operational to deliver stimulation signals 60. Lead diagnostics module 62 can also detect when the therapy lead 38 is not operationally connected to the therapy module 58. The therapy lead 38 has a proximal end with a therapy lead connector 76, and the therapy lead connector 76 is configured to couple with the therapy module connector 74 and the lead diagnostic module 62. The therapy lead 38 includes a stimulation lead 24 and in some embodiments includes a lead extension 22 and in other embodiments includes both a lead extension 22 and a screening cable 36. The therapy lead 38 has a proximal end with a therapy lead connector 76. The therapy lead connector 76 is configured to couple with the therapy module 58 and the lead diagnostics module 62. The therapy lead 38 can become not fully operational or inoperative for a wide variety of reasons such as when the screening cable 36 becomes electrically disconnected from the therapy module connector 74, the screening cable 36 electrical conductors loose continuity, the lead extension 22 becomes electrically disconnected from either the stimulation lead 24 or the screening cable 36 or the TNS 20 depending upon embodiment, the extension lead 22 electrical conductors loose continuity, the stimulation lead 24 electrical conductors loose continuity, or corrosion degrades an electrical connection in the therapy lead 38. The annunciator, annunciates when the therapy lead 38 in not operational to deliver stimulation signal.

Figure 13:
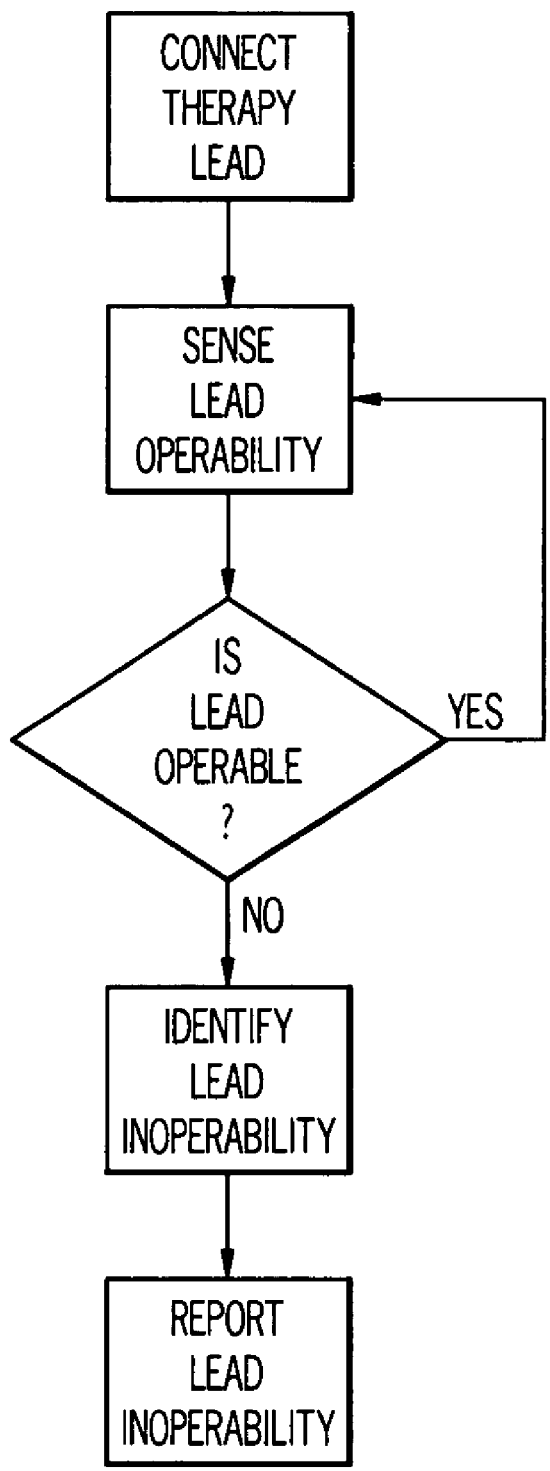
FIG. 13 shows a lead diagnostics module operational flowchart embodiment.

FIG. 12 shows a lead diagnostics module 62 block diagram embodiment, and FIG. 13 shows a lead diagnostics operation flowchart embodiment. The lead diagnostics module 62 is coupled to the therapy module connector 76 and coupleable to a therapy lead 38. The lead diagnostics module 62 senses whether the therapy lead 38 is operable to deliver stimulation signals. If the therapy lead 38 is operable, the lead diagnostics 62 periodically or continuously checks to determine if the therapy lead 38 continues to be operational. If the diagnostics module 62 determines that the therapy lead 38 is not operational to deliver stimulation signals 62, the therapy program can be modified to reduce stimulation shock when the therapy lead 38 becomes operational to delivery stimulation signals 60. Stimulation shock can be reduced by gradually increasing stimulation signal 60 parameters of the therapy program when the therapy lead 38 becomes operational. The lead diagnostics module 62 can be configured in a variety of embodiments including as a lead sensor 76 embodiment, a lead measurement embodiment, or a combination lead sensor and lead measurement embodiment.

Figure 3C:
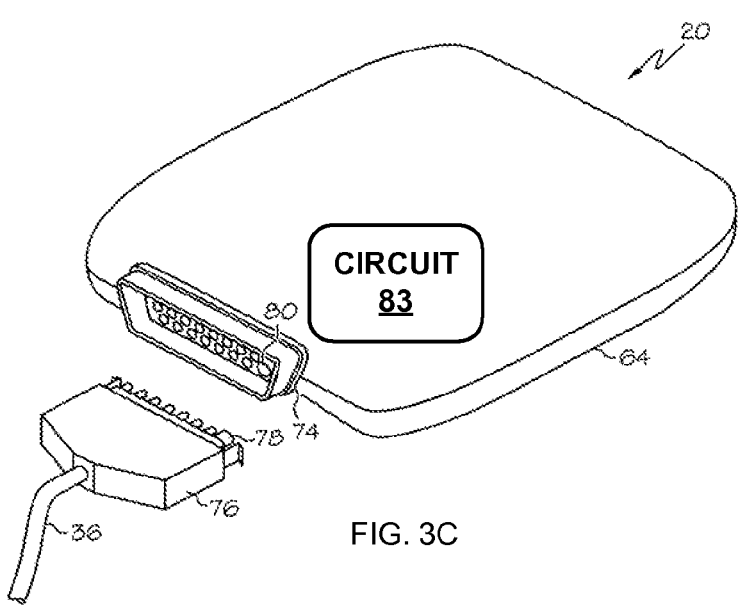
FIG. 3c shows another TNS embodiment.
Figure 14:
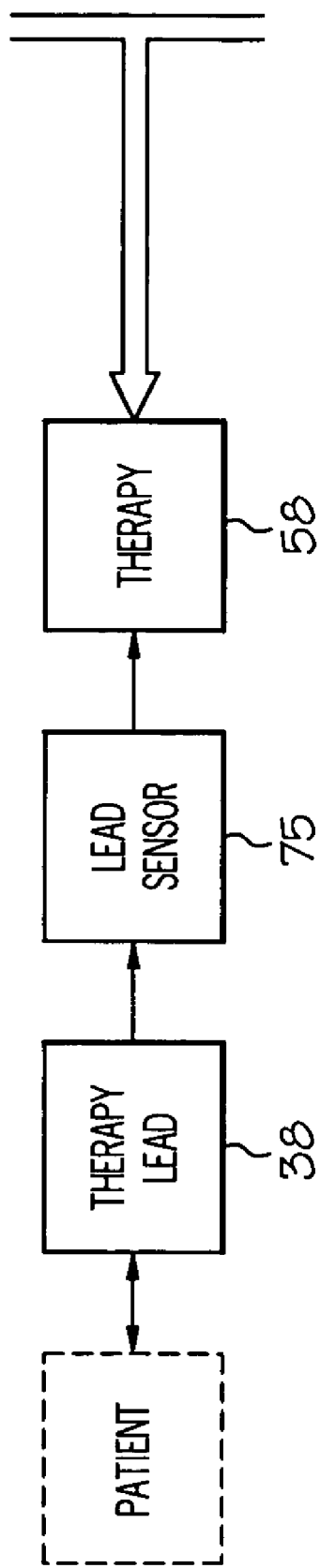
FIG. 14 shows a lead diagnostics lead sensor and related components block diagram embodiment.
Figure 15:
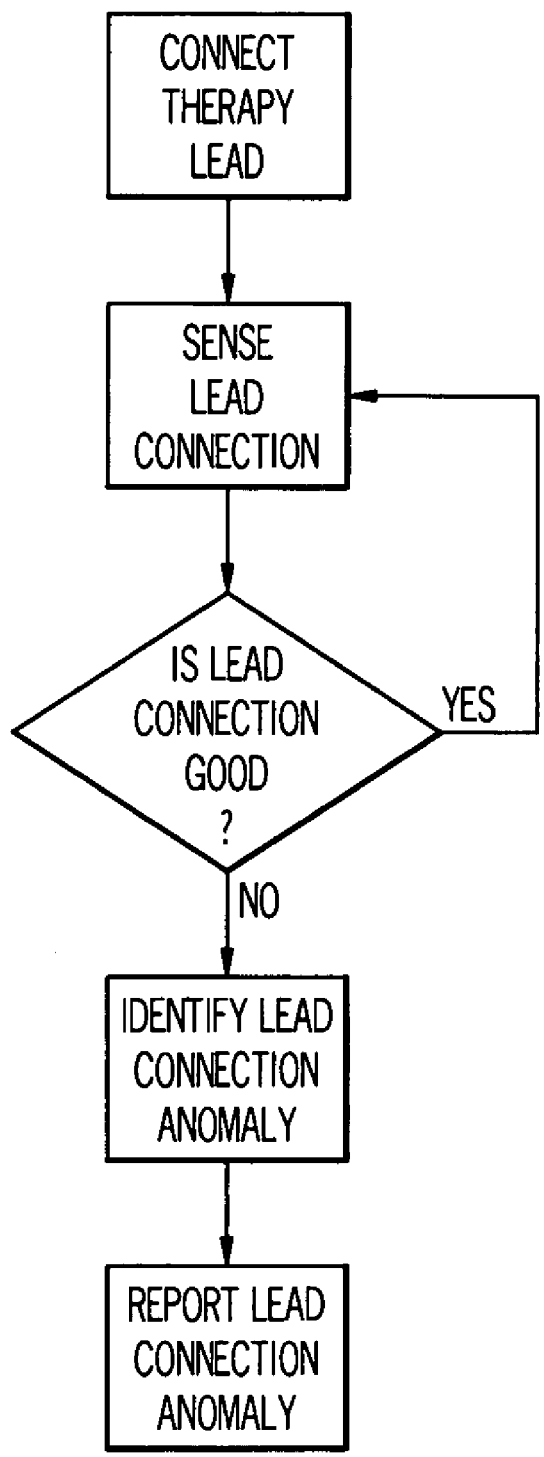
FIG. 15 shows a lead diagnostic lead sensor operation flowchart embodiment.

FIG. 14 shows a lead sensor block diagram embodiment, and FIG. 15 shows a lead sensor flowchart embodiment. The lead sensor 75 can be configured with complimentary details in the therapy lead connector 76 and the therapy module connector 74. The therapy lead connector 76 can have at least one lead sensor detail that mates with at least one therapy module detail carried in the therapy module connector 74 to operate the lead sensor 75. As illustrated in FIG. 3a, the lead sensor 75 detail can be configured as at least one lead connector pin 78 in the therapy lead connector 76 and at least one therapy connector plug 80 configured to receive the lead connector pin 78 in the therapy module connector 74 and detect whether therapy lead connector 76 is operationally connected to the therapy module connector 74. In one embodiment, as further illustrated in FIG. 3a, the lead connector pin 78 can be configured to actuate a switch 82 carried in the trial neuro stimulator 20. In another embodiment the lead connector pin 78 can also be configured to complete a circuit 83 carried in the therapy module connector 74 or, as illustrated in FIG. 3c, the trial neuro stimulator 20. In another embodiment, the lead connector pin 78 can be magnetic and configured to operate a magnetic switch carried in the therapy sensor.

The lead diagnostics module 62 can also be configured as a lead measurement embodiment.

Figure 16:
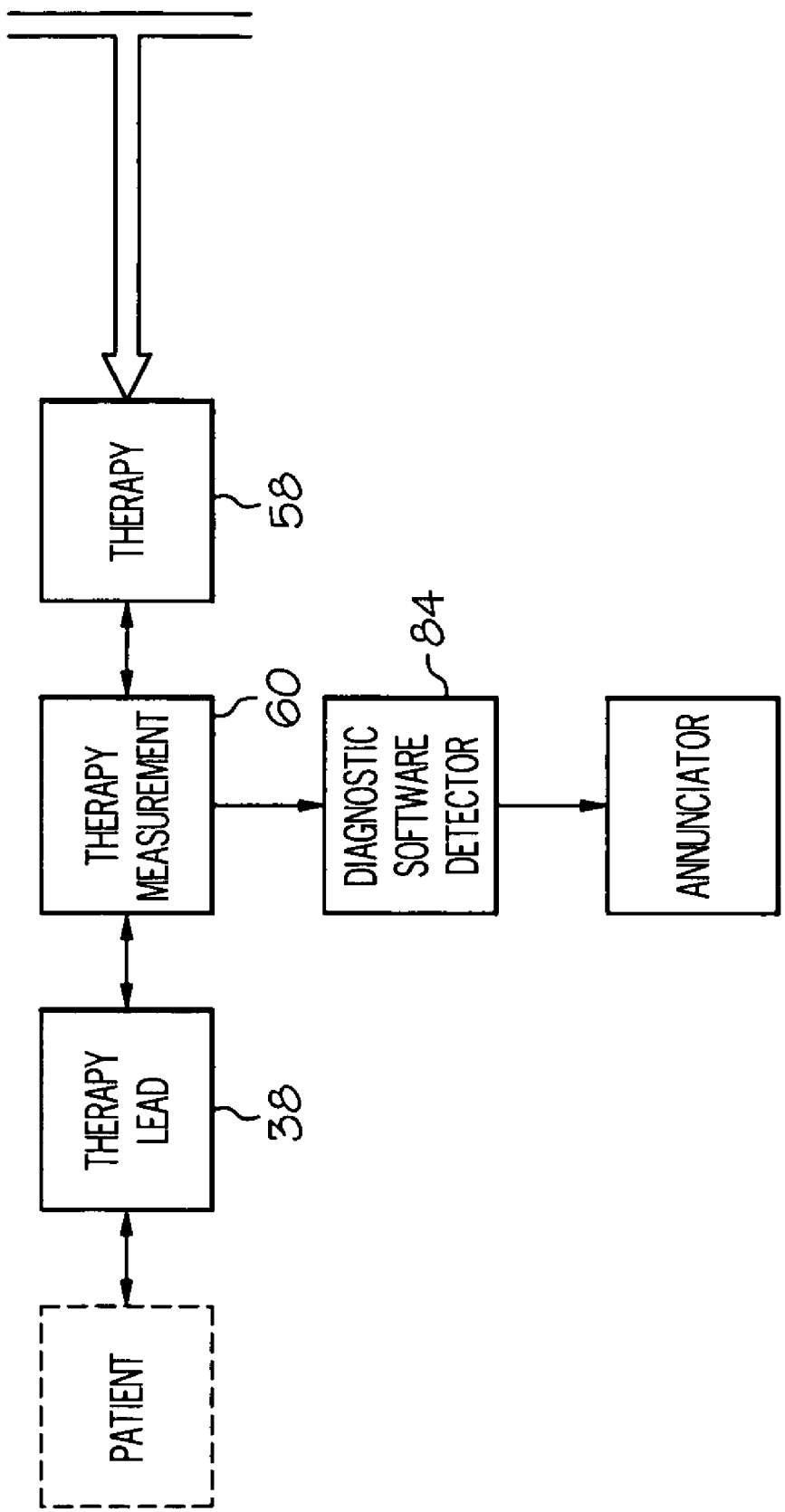
FIG. 16 shows a lead diagnostics software detector and related components block diagram embodiment.
Figure 17:
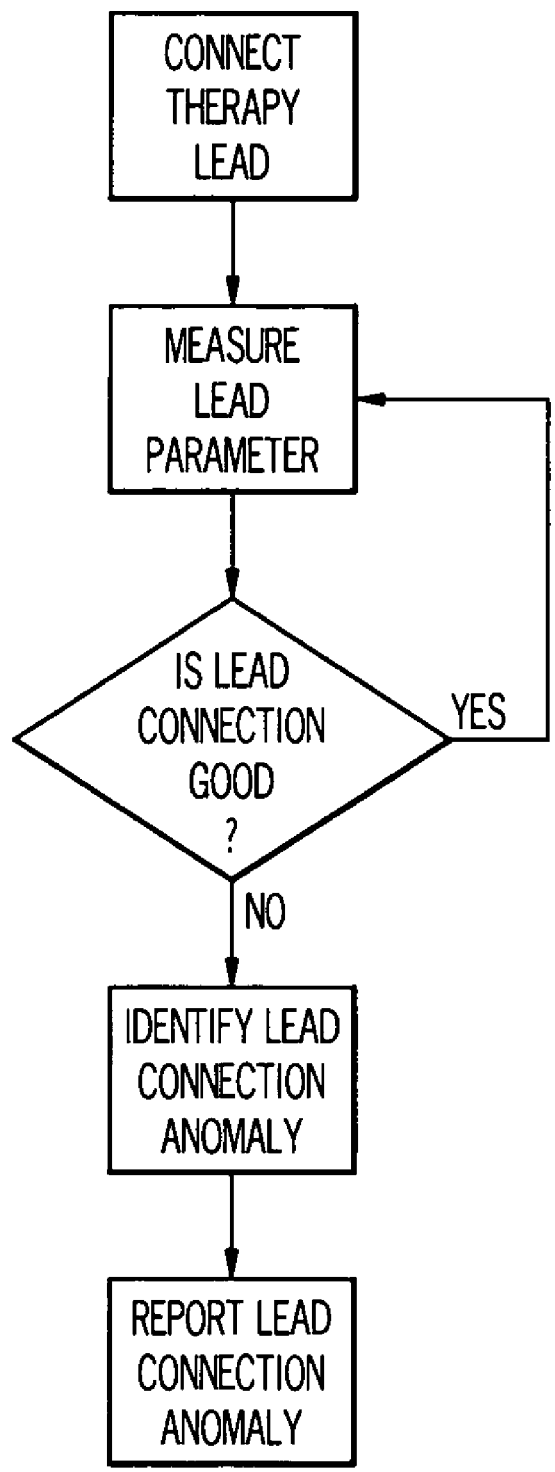
FIG. 17 shows a lead diagnostics software detector operation flowchart embodiment.

FIG. 16 shows a lead measurement block diagram embodiment, and FIG. 17 shows a lead measurement flowchart embodiment The lead diagnostic module 62 includes a software detector 84 that receives therapy lead 38 measurement data from a therapy measurement module.

The therapy lead 38 measurement data is used to determine whether the therapy lead 38 is operational to deliver stimulation signals 60. The therapy measurement data is data that relates to therapy lead integrity such as lead impedance. The lead impedance measurement can be compared against predetermined data such as earlier lead impedance measurements or a predetermined value to detect whether the therapy lead 38 is operational. The lead measurement embodiment can also be used with the sensor embodiment discussed under FIG. 15. When the lead measurement and sensor are used together in an embodiment, the sensor 75 can provide an input to the software detector 84, or the lead measurement embodiment and sensor embodiment can operate independently from one another. Lead diagnostics can also be expressed as a method.

Figure 18:
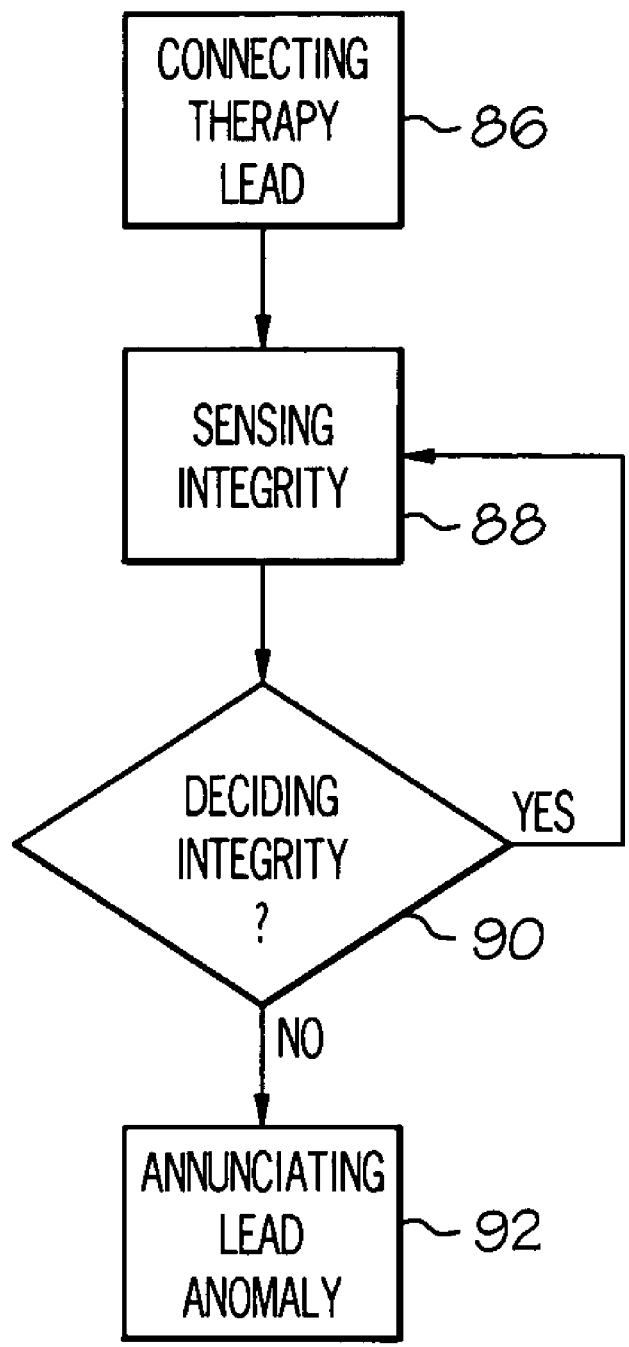
FIG. 18 shows a lead diagnostics operation flowchart embodiment.

FIG. 18 shows a lead diagnostic method embodiment. The method of diagnosing whether a therapy lead is operationally connected to a trial neuro stimulator comprises the following elements. The therapy lead is connected to a therapy connector. The integrity 88 of the connection between the therapy lead 38 and the therapy connector 74 is sensed. The integrity of the connection between the therapy lead 38 and the therapy connector 74 can be sensed with a lead sensor 75, the lead measurements performed by the therapy measurement module 60, or by a combination of the lead sensor 75 and therapy lead 38 measurements. A decision 90 is made whether the integrity of the connection between the therapy lead 38 and the therapy connector 74 is adequate. The decision 90 can be made directly by a lead sensor 75, or by a software detector 84, or by a combination of a lead sensor 75 and a software detector 84. If the decision is that the therapy lead connection is inadequate, then the inadequate condition is annunciated 92 and the therapy can be terminated.

The inadequate condition can be directly annunciated to the patient with a transducer such as a visual, audible, tactile or combination of these transducers. The inadequate condition can also be annunciated directly to INS 20 for one or more actions such as ceasing therapy, modifying the therapy, logging the inadequate condition, and the like. Once the inadequate condition is corrected the therapy program can be modified to gradually increase stimulation signal 60 parameters to the therapy program stimulation signal 60 parameter to reduce stimulation shock. Since nonconformance can be intermittent such that therapy lead only becomes inoperative when the patient makes a particular movement several times a day, modifying the therapy to gradually increase stimulation signal 60 parameter can greatly improve patient comfort and safety.

Thus, a Trial Neuro Stimulator (TNS) 20 with lead diagnostics is disclosed to improve TNS operation in areas such as reliability and patient comfort. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. A trial neuro stimulator with diagnostics for screening a patient to evaluate the efficacy of neuro stimulation comprising:
a processor;
a memory coupled to the processor containing a therapy program;
a therapy module operated according to the therapy program to produce stimulation signals, the therapy module having a therapy module connector that includes at least one therapy connector plug;
a therapy lead having a distal end for implantation in the patient and a proximal end that includes a therapy lead connector, the therapy lead connector configured to couple with the therapy module connector outside of the patient and including at least one lead connector pin that is received by the therapy connector plug;
a lead diagnostic module configured for detecting at least one of an operational disconnection of the therapy lead from the therapy module, degradation of a conductor of the therapy lead, or discontinuity of the conductor of the therapy lead, and determining that the therapy lead is not operational to deliver stimulation signals based on the detection; and
a switch, wherein the lead connector pin actuates the switch, and the lead diagnostic module detects an operational disconnection of the therapy lead from the therapy module by detecting whether the therapy lead connector is operationally connected to the therapy module connector based on actuation of the switch, and
wherein the trial neuro stimulator is configured for ambulatory operation.

2. The trial neuro stimulator of claim 1, further comprising a therapy measurement module, wherein the lead diagnostic module includes a software detector that receives therapy lead measurement data from the therapy measurement module and detects the at least one of the operational disconnection of the therapy lead from the therapy module, degradation of the conductor of the therapy lead, or discontinuity of the conductor of the therapy lead by comparing the therapy lead measurement data to predetermined data.

3. The trial neuro stimulator of claim 2, wherein the therapy measurement module is configured to measure a therapy lead impedance.

4. The trial neuro stimulator of claim 1, further comprising an annunciator to annunciate when the at least one of the operational disconnection of the therapy lead from the therapy module, degradation of the conductor of the therapy lead, or discontinuity of the conductor of the therapy lead is detected.

5. The trial neuro stimulator of claim 1, wherein the therapy lead comprises one of an implanted lead coupled to a percutaneous extension and a percutaneous lead.

6. The trial neuro stimulator of claim 1, wherein the therapy lead includes a screening cable, and a proximal end of the screening cable includes the therapy lead connector.

7. A trial neuro stimulator with diagnostics for screening a patient to evaluate the efficacy of neuro stimulation comprising:
  a processor;
  a memory coupled to the processor containing a therapy program;
  a therapy module operated according to the therapy program to produce stimulation signals, the therapy module having a therapy module connector that includes at least one therapy connector plug;
  a therapy lead having a distal end for implantation in the patient and a proximal end that includes a therapy lead connector, the therapy lead connector configured to couple with the therapy module connector outside of the patient and including at least one lead connector pin that is received by the therapy connector plug;
  a lead diagnostic module configured for determining whether the therapy lead is operational to deliver stimulation signals; and
  a switch, wherein the lead connector pin actuates the switch and the lead diagnostic module determines whether the therapy lead is not operationally connected to the therapy module by detecting whether the therapy lead connector is operationally connected to the therapy module connector based on actuation of the switch.

8. The trial neuro stimulator of claim 7, further comprising a therapy measurement module, wherein the lead diagnostic module includes a software detector that receives therapy lead measurement data from the therapy measurement module, compares the therapy lead measurement data to predetermined data, and determines whether the therapy lead is not operationally connected to the therapy module based on the comparison.

9. A trial neuro stimulator with diagnostics for screening a patient to evaluate the efficacy of neuro stimulation comprising:
  a processor;
  a memory coupled to the processor containing a therapy program;
  a therapy module operated according to the therapy program to produce stimulation signals, the therapy module having a therapy module connector that includes at least one therapy connector plug;
  a therapy lead having a distal end for implantation in the patient and a proximal end that includes a therapy lead connector, the therapy lead connector configured to couple with the therapy module connector outside of the patient and including at least one lead connector pin that is received by the therapy connector plug;
  a lead diagnostic module configured for detecting at least one of an operational disconnection of the therapy lead from the therapy module, degradation of a conductor of the therapy lead, or discontinuity of the conductor of the therapy lead, and determining that the therapy lead is not operational to deliver stimulation signals based on the detection; and
  a circuit, wherein the lead connector pin completes the circuit, and the lead diagnostic module detects an operational disconnection of the therapy lead from the therapy module by determining whether the therapy lead connector is operationally connected to the therapy module connector based on completion of the circuit, and
  wherein the trial neuro stimulator is configured for ambulatory operation.

10. A trial neuro stimulator with diagnostics for screening a patient to evaluate the efficacy of neuro stimulation comprising:
  a processor;
  a memory coupled to the processor containing a therapy program;
  a therapy module operated according to the therapy program to produce stimulation signals, the therapy module having a therapy module connector that includes at least one therapy connector plug;
  a therapy lead having a distal end for implantation in the patient and a proximal end that includes a therapy lead connector, the therapy lead connector configured to couple with the therapy module connector outside of the patient and including at least one lead connector pin that is received by the therapy connector plug;
  a lead diagnostic module configured for determining whether the therapy lead is operational to deliver stimulation signals; and
  a circuit, wherein the lead connector pin completes the circuit and the lead diagnostic module determines whether the therapy lead is not operationally connected to the therapy module by detecting whether the therapy lead connector is operationally connected to the therapy module connector based on completion of the circuit.

11. A medical device comprising:
  a processor;
  a memory coupled to the processor containing a therapy program;
  a therapy module operated according to the therapy program to produce stimulation signals, the therapy module having a therapy module connector that includes at least one therapy connector plug;
  a therapy lead having a distal end for implantation in the patient and a proximal end that includes a therapy lead connector, the therapy lead connector configured to couple with the therapy module connector outside of the patient and including at least one lead connector pin that is received by the therapy connector plug;
  a lead diagnostic module configured for detecting at least one of an operational disconnection of the therapy lead from the therapy module, degradation of a conductor of the therapy lead, or discontinuity of the conductor of the therapy lead, and determining that the therapy lead is not operational to deliver stimulation signals based on the detection; and
  a switch, wherein the lead connector pin actuates the switch and the lead diagnostic module detects an operational disconnection of the therapy lead from the therapy module by detecting whether the therapy lead connector is operationally connected to the therapy module connector based on actuation of the switch.

12. A medical device comprising:
  a processor;
  a memory coupled to the processor containing a therapy program;
  a therapy module operated according to the therapy program to produce stimulation signals, the therapy module having a therapy module connector that includes at least one therapy connector plug;

a therapy lead having a distal end for implantation in the patient and a proximal end that includes a therapy lead connector, the therapy lead connector configured to couple with the therapy module connector outside of the patient and including at least one lead connector pin that is received by the therapy connector plug;

a lead diagnostic module configured for detecting at least one of an operational disconnection of the therapy lead from the therapy module, degradation of a conductor of the therapy lead, or discontinuity of the conductor of the therapy lead, and determining that the therapy lead is not operational to deliver stimulation signals based on the detection; and a circuit, wherein the lead connector pin completes the circuit and the lead diagnostic module detects an operational disconnection of the therapy lead from the therapy module by determining whether the therapy lead connector is operationally connected to the therapy module connector based on completion of the circuit.

* * * * *